US008501431B2

(12) United States Patent
Terrero et al.

(10) Patent No.: US 8,501,431 B2
(45) Date of Patent: Aug. 6, 2013

(54) METHOD FOR SCREENING FOR COMPOUNDS SELECTIVELY INTERACTING WITH RAD9

(75) Inventors: David Terrero, Ensanche Quisquella (DO); Federico M. Gomez, Boca Raton, FL (US); C. Federico Gomez Garcia-Godoy, Santo Domingo (DO)

(73) Assignee: Magnachem International Laboratories, Inc., Boca Raton, FL (US)

( * ) Notice: Subject to any disclaimer, the term of this patent is extended or adjusted under 35 U.S.C. 154(b) by 610 days.

(21) Appl. No.: 12/605,896

(22) Filed: Oct. 26, 2009

(65) Prior Publication Data

US 2010/0137618 A1 Jun. 3, 2010

Related U.S. Application Data

(60) Provisional application No. 61/108,224, filed on Oct. 24, 2008.

(51) Int. Cl.
*C12Q 1/02* (2006.01)
(52) U.S. Cl.
USPC ............... 435/29; 435/6.1; 435/325; 549/313
(58) Field of Classification Search
USPC .............................. 435/6.1, 29, 325; 549/313
See application file for complete search history.

(56) References Cited

U.S. PATENT DOCUMENTS

| | | | |
|---|---|---|---|
| 2,624,723 A | 1/1953 | McGraw et al. | |
| 3,203,953 A | 8/1965 | Lucas et al. | |
| 3,210,377 A | 10/1965 | Machleidt et al. | |
| 3,993,771 A | 11/1976 | Uematsu et al. | |
| 4,001,425 A | 1/1977 | Price, Jr. | |
| 4,613,613 A | 9/1986 | Oguri et al. | |
| 5,242,945 A | 9/1993 | Caufield et al. | |
| 5,250,735 A | 10/1993 | Wong et al. | |
| 5,281,622 A | 1/1994 | Wong et al. | |
| 5,595,756 A | 1/1997 | Bally et al. | |
| 5,646,164 A | 7/1997 | Tzeng et al. | |
| 5,905,089 A | 5/1999 | Hwang et al. | |
| 5,962,460 A | 10/1999 | Tzeng et al. | |
| 5,977,169 A | 11/1999 | Chrusciel et al. | |
| 5,981,575 A | 11/1999 | Kuhajda | |
| 6,180,651 B1 | 1/2001 | Nicolai et al. | |
| 6,222,048 B1 | 4/2001 | Black et al. | |
| 6,232,474 B1 | 5/2001 | Brandenburg et al. | |
| 6,395,724 B1 | 5/2002 | Judice et al. | |
| 6,686,390 B2 | 2/2004 | Pal et al. | |
| 6,900,242 B2 | 5/2005 | Terrero | |
| 7,323,495 B2 | 1/2008 | Terrero | |
| 2004/0208944 A1 | 10/2004 | Malnoe | |
| 2005/0101663 A1 | 5/2005 | Terrero | |
| 2005/0209316 A1* | 9/2005 | Terrero | 514/469 |
| 2008/0125484 A1 | 5/2008 | Terrero | |

FOREIGN PATENT DOCUMENTS

| | | |
|---|---|---|
| EP | 0 534 907 | 3/1993 |
| EP | 0 712 843 | 11/1999 |
| JP | 51-125722 | 11/1976 |
| JP | 54-084564 | 7/1979 |
| JP | 56-128776 | 10/1981 |
| JP | 58-099413 | 6/1983 |
| JP | 62-026221 | 2/1987 |
| JP | 64-016776 | 1/1989 |
| JP | 01-163175 | 6/1989 |
| JP | 2002-37797 A2 | 2/2002 |
| WO | WO 96/29392 | 9/1996 |
| WO | 9718806 | 5/1997 |
| WO | WO 97/28147 | 8/1997 |
| WO | 9843966 | 10/1998 |
| WO | WO 99/53915 | 10/1999 |
| WO | WO 01/064913 | 9/2001 |

OTHER PUBLICATIONS

Simon et al., "Differential Toxicities of Anticancer Agents among DNA repair and Checkpoint Mutants of *Saccharomyces cerevisiae*", Cancer Research, 2000, vol. 60, pp. 328-333.*
Adam, et al., "Stereoelectronic control 1,3 of the diastereoselectivity in the photooxygenation (Schenck Ene Reaction) of an electron-poor allylic alchohol and its ethers", *J. Org. Chem.*, 63(2):226-227 (1998).
Baldwin, et al., 5-endo-Trigonal reactions: a disfavoured ring closure, *J. Chem. Soc. Chem. Comm.*, 18:736-38 (1976).
Burke and Pacofsky, "The ester enolate claisen rearrangement", *Tetrahedron Lett.*, 27(4):445-448 (1986).
Burke, et al., "Synthesis or ethisolide, isoavenaciolide and avenciolide", *J. Org. Chem.*, 57(8):2228-2235 (1992).
Burtelow, et al., "Reconstitution and molecular analysis of the hRad9-hHus1-hRad1 (9-1-1) DNA damage responsive checkpoint complex," *J. Biol. Chem.*, 276(28):25903-9 (2001).
Caspari, et al., "Characterization of *Schizosaccharomyces pombe* Hus1: a PCNA-related protein that associates with Rad1 and Rad9," *Mol. Cell. Biol.*, 20(4):1254-62 (2000).
Cassady, et al., "Potential antitumor agents. Synthesis, reactivity, and cytoxicity of alpha-methylene carbonyl compounds", *J. Med. Chem.*,21(8):815-9 (1978).
Cavallito and Haskell, "α-methylene butyrolactone from Erythronium anerucanum", *J. Am. Chem. Soc.*, 68 (11), pp. 2332-2334 (1946).
Chen, et al., "Cytotoxic butanolides from Litsea Akoensis", *Phytochemistry*, 49(3):745-50 (1998).

(Continued)

*Primary Examiner* — Susan Hanley
(74) *Attorney, Agent, or Firm* — Pabst Patent Group LLP

(57) ABSTRACT

Natural and synthetic compounds of Formulae Ia-Ie having a lactone structure, in particular Securolide, have been determined to be effective anti-tumor compounds which target the hrad9 gene and/or protein encoded thereby or complex containing the protein and/or the p53 gene and/or protein. Securolide is cytoselective for mutants of hRad9 based on studies conducted in Rad9 mutant yeast strains. Securolide appears to interact with mutant hRad9 in cancer cells to produce DNA lesions which result in apoptosis. Studies have demonstrated that Securolide is useful for treating proliferation disorders such as melanoma, leukemia, breast cancer, lung cancer, ovarian cancer, colon cancer, esophagus cancer, liver cancer, and lymphatic cancer, and to alleviate pain associated with the cancer. Other compounds effective for the treatment of cancer and optionally pain associated therewith may also be identified using the same assays, for example, by screening for efficacy in assays using Rad9 and/or p53 defective mutant yeasts.

6 Claims, No Drawings

OTHER PUBLICATIONS

Chen, et al., "α-Methylene-γ-butyrolactones: synthesis and vasorelaxing activity assay of coumarin, naphthalene, and quinolone derivatives", *Chem. Pharm. Bull.*, 46(6): 962-965 (1998).

Corbet and Benezra, "Allergenic alpha-methylene-gamma-lactones", *J. Org. Chem.*, 46(6):1141-1147 (1981).

Fuchino, et al., "New sesquiterpene lactones from *Elephantopus mollis* and their leishmanicidal activities", *Planta Me*, 67:647-653 (2001).

Gelin and Chantegrel, "Synthesis of 3-Formyltetronic acid and enamine derivatives", *J. Heterocyclic Chem.*, 18:663-665 (1981).

Grigg, et al., "X=Y-ZH Systems as potential 1,3-dipoles part 35. Generation of nitrones from oximes. Class 3 processes. Tandem intramolecular Michael addition (1,3-azaprotio cyclotransfer)-intermolecular 1,3-dipolar cycloaddition reactions." *Tetrahedron*, 48(33): 6929-6952 (1992).

Hall, et al., Anti-inflammatory activity of sesquiterpene lactones and related compounds, *J. Pharm. Sci.*, 68(5):537-42 (1979).

Hartwell, et al., "Cell cycle control and cancer," *Science*, 266(5192):1821-8 (1994).

Hartwell, et al., "Checkpoints: controls that ensure the order of cell cycle events," *Science*, 246(4930):629-34 (1989).

Hein, et al., "Bombardolides: new antifungal and antibacterial gamma-lactones from the coprophilous fungus *Bombardioidea anartia*", *J. Nat. Prod.*, 64(6):809-12 (2001).

Hidaka, et al., "Inhibition of polymorphonuclear leukocyte 5-lipoxygenase and platelet cyclooxygenase by alpha-(3,5-di-tert-butyl-4-hydroxybenzylidene)-gamma-butyrolactone (KME-4), a new anti-inflammatory drug", *Jpn. J. Pharmacol.*, 38(3):267-72 (1985).

Hoffmann and Rabe, "Synthese und biologische activitat von α-methylen-γ-butyrolactonen," *Angewandte Chemie*, 97(2):96-112 (1985).

Howie, et al., "Synthesis of alkyl-substituted αβ-unsaturated γ-lactones as potential antitumor agents," *J. Med. Chem.*, 17(8):840-3 (1974).

Huang, et al., "Synthetic and cytotoxic studies of α-methylene-γ-butyrolactone bearing pyrimidines", *Kaohsiung J. Med Sci.*, 9:707-711 (1993).

Humphrey, "DNA damage and cell cycle control in *Schizosaccharomyces pombe*," *Mutat. Res.*, 451(1-2):211-26 (2000).

Hutchinson, "A synthesis of tulipalin A and B and the acylglucoside, tuliposide A, fungitoxic agents from *Tulipa gesneriana*. Carbon-13 nuclear magnetic resonance analysis of anomeric configuration in acylglucosides", *J. Org. Chem.*, 39(13):1854-8 (1974).

Ingolfsdottir, et al., "In vitro susceptibility of Helicobacter pylori to protolichesterinic acid from the lichen *Cetraria islandica*" *Antimicrob. Agents Chemother.* 1997 41(1):215-7 (1997).

Kuhajda, et al., "Synthesis and antitumor activity of an inhibitor of fatty acid synthase", *Proc. Natl. Acad. Sci. USA*, 97(7):3450-3454 (2000).

Kunes, et al., "Synthesis and antifungal activity evaluation of 3-hetaryl-2,5-dihydrofuran-2-ones", *Collect. Czech. Chem. Commun.*, 66:1809-1830 (2001).

Kwon, et al., "New cytotoxic butanolides from *Lindera obtusiloba* BLUME", *Chem. Pharm. Bull. (Tokyo).*, 48(5):614-6 (2000).

Lee, et al., "Sesquiterpene antitumor agents: inhibitors of cellular metabolism", *Science*, 196:533-535 (1977).

Lee, et al., "Synthesis and anticancer evaluation of certain α-methylene-γ-(4-substituted phenyl)-γ-butyrolactone bearing thymine, uracil, and 5-bromouracil", *Bioorg. Med. Chem.*, 9:241-244 (1999).

Lenz, et al., "A test battery of bacterial toxicity assays and comparison of $LD_{50}$ values," *Toxicity Assessment*, 4(1):43-52 (1989).

Maria, et al., "Gastric anti-ulcer activity of several α,β-unsaturated carbonyl compounds in rats", *Biol. Pharm. Bull.*, 23(5):555-557 (2000).

Mossi, et al., "Clamping down on clamps and clamp loaders—the eukaryotic replication factor C," *Eur. J. Biochem.*, 254(2):209-16 (1998).

Murray and Norton, "The design and mechanism of palladium catalysts for synthesis of methylene lactones by cyclocarbonylation of acetylenic alcohols", *J. Am. Chem. Soc.*, 101:4107-19 (1979).

Nishide, et al., "Total asymmetric syntheses of (+)-blastomycinone and related gamma-lactones", *Tetrahedron*, 50(28):8337-8338 (1994).

Nojima, "Cell cycle checkpoints, chromosome stability and the progression of cancer," *Hum. Cell*, 10(4):221-30 (1997).

Panda, et al., "Mechanism of action of alpha-methylene-gamma-lactone derivatives of substituted nucleic acid bases in tumour cells", *Chemotherapy*, 35:174-180 (1989).

Park, et al., "Anti-helicobacter pylori effect of costunolide isolated from the stem bark of *Magnolia sieboldii*," *Arch. Pharm. Res.*, 20(3):275-279 (1997).

Paulitz, et al., "A novel antifungal furanone from *Pseudomonas aureofaciens*", *J. Chem. Eco.*, 26(6):1515-1524 (2000).

Pour, et al., "3-Phenyl-5-methyl-2H,5H-furan-2-ones: tuning antifungal activity by varying substituents on the phenyl ring", *Bioorg. Med Chem. Lett.*, 10(16):1893-5 (2000).

Prestera, et al., "Chemical and molecular regulation of enzymes that detoxify carcinogens", *Proc. Natl. Acad. Sci. U. S. A.*, 90(7):2965-9 (1993).

Rezanka and Dembitsky, "gamma-Lactones from the soft corals *Sarcophyton trocheliophorum* and *Lithophyton arboreum*", *Tetrahedron*, 57(41):8743-8749 (2001).

Rodriguez, et al., "Biological activities of sesquiterpene lactones", *Phytochemistry*, 15:1573-1580 (1976).

Rollinson, et al., "The total synthesis of Lauraceae lactones", *J. Am. Chem. Soc.*, 103(14):4114-4125 (1981).

Sanyal, et al., "New α-methylene-γ-lactone derivatives of substituted nucleic acid bases as potential anticancer agents", *J. Med. Chem.*, 29(5):595-599 (1986).

Schlewer, et al., "Synthesis of α-methylene-γ-butyrolactones: a structure-activity relationship study of their allergenic power", *J. Med. Chem.*, 23:1031-1038 (1980).

Schuster, et al., "Sesquiterpene lactones from *Koanophyllon albicaule*", *Pytochemistry*, 31(9):3143-6 (1992).

Spring, et al., "Annuithrin, a new biologically active germacranolide from *Helianthus annuus*", *Phytochemistry*, 20(8):1883-1885 (1981).

St.Onge, et al., "A Role for the Phosphorylation of hRad9 in Checkpoint Signaling," *J. Biol. Chem.*, 276:41898-905 (2005).

Su and Tamm, "Synthesis studies towards Pseurotin A", *Helvet. Chim. Acta.*, 78:1278-1290 (1995).

Sussmuth, et al., "Effects of test conditions and interfering factors on sensitivity of bacterial tests based on inhibition of growth and motility," *Environmental Toxicology and Water Quality*, 7(3):257-74 (1992).

Tsai, et al., "Cytotoxic butanolides from the stem bark of Formosan *Lindera communis*", *Planta Med.*, 67(9):865-7 (2001).

Venclovas, et al., "Structure-based predictions of Rad1, Rad9, Hus1 and Rad17 participation in sliding clamp and clamp-loading complexes," *Nucleic Acids Res.*, 28(13):2481-93 (2000).

Vilella, et al., "Inhibitors of farnesylation of Ras from a microbial natural products screening program," *J. Ind. Microbiol. Biotechnol.*, 25(6):315-327 (2000).

Viturro, et al., "Antifungal diastereomeric furanones from *Mutisia friesiana*: structural determination and conformational analysis", *Tetrahedron. Asymm.*, 12(7):991-998 (2001).

Weinert, "DNA damage checkpoints update: getting molecular," *Curr. Opin. Genet. Dev.*, 8(2):185-93 (1998).

Willuhn, "*Arnica* flowers: pharmacology, toxicology, and analysis of the sesquiterpene lactones—their main active substance," in *Phytomedicines of Europe: Chemistry and Biological Activity* (Lawson, et al, eds.) Washington DC American Chemical Society, pp. 118-132 (1997).

Wong, *Chinese J. of Medic. Chem.*, 4(2): 137-149 (1994).

Zampella, et al., "Amphiastemins: a new family of cytotoxic metabolites from the marine sponge Plakortis quasiamphiaster", *Tetrahedron*, 57(1):257-263 (2001).

Zapf, et al., "Incrusoporin, a new antibiotic from *Incrustoporia carneola*", *Acta. Chem. Scand.*, 49:233-34 (1995).

Benezra, "Molecular recognition in allergic contact dermatitis to natural products", Pure & Appl. Chem, 62(7):1251-58 (1990).

Chan, "Mechanisms of Renal Allograft Rejection," *Transplant rejection and its Treatment* (Tracy 12), Dec. 12, 2008.

Meyerkord, et al., "Loss of Hus 1 sensitizes cells to etoposide-induced apoptosis by regulating Bh3-only proteins." *Oncogene*, 27(58): 7248-7259 (2008).

Strome, et al., "Heterozygous screen in *Saccharomyces cerevisiae* identifies dosage-sensitive genes that affect chromosome stability." *Genetics*, 178(3): 1193-1207 (2008).

Hopkins, et al., "Deletion of mouse rad9 causes abnormal cellular responses to DNA damage, genomic instability, and embryonic lethality." *Molecular and Cellular Biology*, 24(16): 7235-7248 (2004).

Mon, et al., "Novel approaches to screen for anticancer drugs using *Saccharomyces cerevisiae,*", *Methods in Molecular Biology*, 223: 555-576 (2003), Simon et al.

Julian, et al., "Novel approaches to screen for anticancer drugs using *Saccharomyces cerevisiae*", Meth. Mol. Biol., 223:555-76 (2004).

\* cited by examiner

METHOD FOR SCREENING FOR COMPOUNDS SELECTIVELY INTERACTING WITH RAD9

CROSS REFERENCE TO RELATED APPLICATIONS

This application claims priority to U.S. Ser. No. 61/108,224 "Method for Screening for Compounds Selectively Interacting with RAD9" by David Terrero, filed on Oct. 24, 2008.

FIELD OF THE INVENTION

The present invention is generally in the field of targets for anti-cancer compounds, and methods of screening therefore.

BACKGROUND OF THE INVENTION

Many compounds are known for the treatment of cancer. Most act via inhibition of DNA replication or cell proliferation, in general, and are not specific for transformed cells. Although specificity has been imparted through the use of targeting ligands, and binding to specific receptors on the tumor cells, in general most anti-tumor compounds are effective by virtue of killing more of the more rapidly proliferating tumor cells as compared to the more slowly replicating normal cells.

It would be highly desirable to have more selective compounds, that are cytotoxic to tumor cells but not to normal cells.

It is therefore an object of this invention to provide a method for identifying compounds that exhibit selective anti-tumor activity.

It is still further an object of this invention to provide a new class of compounds which exhibit anti-tumor activity through the targeting of the hRad9 gene in humans.

SUMMARY OF THE INVENTION

Natural and synthetic compounds of Formulae Ia-Ie, or metabolites thereof, having a lactone structure, in particular Securolide, have been determined to be highly effective anti-tumor compounds which target the hrad9 gene and/or protein encoded thereby or complex containing the protein and/or the p53 gene and/or protein encoded thereby. Securolide is cytoselective for mutants of hRad9 based on studies conducted in Rad9 mutant yeast strains. Securolide appears to interact with mutant hRad9 in cancer cells to produce DNA lesions which result in apoptosis. Studies have demonstrated that Securolide is useful for treating proliferation disorders such as melanoma, leukemia, breast cancer, lung cancer, ovarian cancer, colon cancer, esophagus cancer, liver cancer, and lymphatic cancer, and to alleviate pain associated with the cancer. Other compounds effective for the treatment of cancer and optionally pain associated therewith may also be identified using the same assays as were used to demonstrate the mechanism of action of Securolide, for example, by screening for efficacy in assays using Rad9 defective mutant yeasts.

DETAILED DESCRIPTION OF THE INVENTION

Definitions

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., C1-C30 for straight chain, C3-C30 for branched chain), preferably 20 or fewer, preferably 10 or fewer, more preferably 6 or fewer, most preferably 5 or fewer. If the alkyl is unsaturated, the alkyl chain generally has from 2-30 carbons in the chain, preferably from 2-20 carbons in the chain, preferably from 2-10 carbons in the chain, more preferably from 2-6 carbons, most preferably from 2-5 carbons. Likewise, preferred cycloalkyls have from 3-20 carbon atoms in their ring structure, preferably from 3-10 carbons atoms in their ring structure, most preferably 5, 6 or 7 carbons in the ring structure. Examples of saturated hydrocarbon radicals include, but are not limited to, methyl, ethyl, n-propyl, isopropyl, n-butyl, t-butyl, isobutyl, sec-butyl, cyclohexyl, (cyclohexyl)methyl, cyclopropylmethyl, and homologs and isomers of, for example, n-pentyl, n-hexyl, n-heptyl, n-octyl. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, and 3-butynyl.

The term "alkyl" includes one or more substitutions at one or more carbon atoms of the hydrocarbon radical as well as heteroalkyls. Suitable substituents include, but are not limited to, halogens, such as fluorine, chlorine, bromine, or iodine; hydroxyl; —$NR_1R_2$, wherein $R_1$ and $R_2$ are independently hydrogen, alkyl, or aryl, and wherein the nitrogen atom is optionally quaternized; —SR, wherein R is hydrogen, alkyl, or aryl; —CN; —$NO_2$; —COOH; carboxylate; —COR, —COOR, or —$CONR_2$, wherein R is hydrogen, alkyl, or aryl; azide, aralkyl, alkoxyl, imino, phosphonate, phosphinate, silyl, ether, sulfonyl, sulfonamido, heterocyclyl, aromatic or heteroaromatic moieties, —CF3; —CN; —$NCOCOCH_2CH_2$; —NCOCOCHCH; —NCS; and combinations thereof.

"Aryl", as used herein, refers to $C_5$-$C_{10}$-membered aromatic, heterocyclic, fused aromatic, fused heterocyclic, biaromatic, or biheteroocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF3, —CN; and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined above for "aryl".

The terms "alkenyl" and "alkynyl" refer to unsaturated aliphatic groups analogous in length and possible substitution to the alkyls described above, but that contain at least one double or triple bond respectively.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

"Alkoxy", "alkylamino", and "alkylthio" are used to refer to those alkyl groups attached to the remainder of the molecule via an oxygen atom, an amino group, or a sulfur atom, respectively.

"Alkylaryl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, $(_{C1-10})$alkyl, phenyl or benzyl, and optionally containing 1-3 double bonds and optionally substituted with one or more substituents. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Heterocyclic groups can optionally be substituted with one or more substituents as defined above for alkyl and aryl.

"Halogen", as used herein, refers to fluorine, chlorine, bromine, or iodine.

Mechanism of Action

Cell cycle checkpoints regulate the precise order of cell cycle events, thus ensuring the distribution of complete copies of the genome to daughter cells (Hartwell, L. & Weinert, T., *Science* 246, 629-634, 1989). Defects in checkpoints lead to genomic instability, a major contributory factor in the development of cancer, because cells with faulty checkpoints proceed into mitosis with damaged or incompletely replicated DNA (Hartwell, L. H. & Kastan, M. B., *Science* 266, 1821-1828, 1995; Nojima, H. *Hum. Cell* 10, 221-230, 1997).

Molecular and genetic studies in the yeasts *Saccharomyces cerevisiae* and *Schizosaccharomyces pombe* have identified an intricate network of genes required for the S-G2/M checkpoint, which ensures cell cycle arrest in response to DNA damage and/or incomplete DNA replication (Weinert, T., *Curr. Opin. Genet. Dev.* 8, 185-193, 1998). In fission yeast, a group of six nonessential checkpoint rad proteins, Hus1, Rad1, Rad3, Rad9, Rad17, and Rad26, constitute the sensory machinery of fission yeast checkpoint cascade (Humphrey, T., *Mutat. Res.* 451, 211-226, 2000). These proteins are required for cell cycle arrest in response to the inhibition of DNA synthesis by compounds such hydroxyurea or DNA damages caused by UV and gamma radiation (Humphrey, T., *Mutat. Res.* 451, 211-226, 2000). These proteins have been highly conserved during evolution, and related proteins have been found in many other eukaryotes, including humans (Venclovas, C. & Thelen, M. P. *Nucleic Acids Res.* 28, 2481-2493, 2000). The human analogs of these checkpoint rad proteins are referred to as hHus1, hRad1, hRad3, hRad9, and hRad17. Rad26 does not have a homolog in humans.

hRad9 interacts with hRad1 and hHus1 in a stable complex that has been dubbed the 9-1-1-complex (Burtelow et al., *J. Biol. Chem.*, 276, 25903-25909, 2001). Structural homology between each member of the 9-1-1 complex and the replication processivity factor proliferating cell nuclear antigen (PCNA) has led to the hypothesis that the 9-1-1 complex replaces replication associated PCNA-dependent functions during DNA repair (Caspari et al., *Mol. Cell. Biol.*, 20, 1254-1262, 2000). During DNA replication, the PCNA homotrimer forms a ring-like sliding clamp over DNA and acts to increase the processivity of DNA polymerase. The 9-1-1/PCNA model is supported by the observation that hRad9, hRad1, and hHus1 each interact with hRad17, which shares extensive homology to subunits of replication factor C, a protein required for loading PCNA[1] onto DNA (Mossi, R, and Hubscher, U., *Eur. J. Biochem.*, 254, 209-216, 1998). Further studies have shown that DNA damage induces not only hyperphosphorylation of hRad9 and hRad1 but also the association of the 9-1-1 complex with chromatin. From this, a model has emerged in which hRad17-dependent loading of 9-1-1 onto DNA at sites of damage could coordinate a multi-faceted checkpoint response (St. Onge et al., *J. Biol. Chem.*, 276, 41898-41905, 2001).

Biomolecular studies in vitro and experimental models suggest that 4,5-dihydro-3-methylene-2[3H]furanone, "Securolide" binds to intracellular structures to trigger intrinsic immune regulators that prevent the growth of aberrant cells. Securolide results in cell death of Rad9 mutant yeast strains. Based on this data, it is believed that Securolide interacts with mutant hRad9 in cancer cells to produce DNA lesions which lead to apoptosis. Bioassays involving mutant strains of *Saccharomyces cereviseae* showed cytotoxicity only on the mutant strains and more specifically to the rad9 gene. This suggests that Securolide has selective cytotoxicity on unstable genomes. Human clinical trials have demonstrated that the in vitro assays are predictive of efficacy in the treatment of cancer and other disease, including patients with breast and prostate cancer who had failed conventional chemotherapy and radiation therapy.

Damaged DNA in *S. cereviseae* activates the gene rad9, which is known as a cell cycle repair checkpoint protein, to arrest the cell cycle after damage has occurred. Rad9 may also promote pro-apoptosis (cell suicide) and suppress cell division. Bioassays show that Securolide causes injuries to damaged DNA through rad9. Hrad9 is the homolog of rad9 in human tumor cells. Since Securolide is cytotoxic to rad9 mutants in other types of yeasts, it is expected that Securolide targets hrad9 in humans to destabilize the genomes of malignant cells.

The p53 gene is a tumor suppressor gene, i.e., its activity stops the formation of tumors. If a person inherits only one functional copy of the p53 gene from their parents, they are predisposed to cancer and usually develop several independent tumors in a variety of tissues in early adulthood. This condition is rare, and is known as Li-Fraumeni syndrome. However, mutations in p53 are found in most tumor types, and so contribute to the complex network of molecular events leading to tumor formation.

The p53 gene has been mapped to chromosome 17. In the cell, p53 protein binds DNA, which in turn stimulates another gene to produce a protein called p21 that interacts with a cell division-stimulating protein (cdk2). When p21 is complexed with cdk2 the cell cannot pass through to the next stage of cell division. Mutant p53 can no longer bind DNA in an effective way, and as a consequence the p21 protein is not made available to act as the 'stop signal' for cell division. Thus cells divide uncontrollably, and form tumors.

p53 becomes activated in response to myriad stress types, which include but is not limited to DNA damage (induced by either UV, IR, or chemical agents such as hydrogen peroxide), oxidative stress, osmotic shock, ribonucleotide depletion and deregulated oncogene expression. This activation is marked by two major events. Firstly, the half-life of the p53 protein is increased drastically, leading to a quick accumulation of p53 in stressed cells. Secondly, a conformational change forces p53 to take on an active role as a transcription regulator in these cells. The critical event leading to the activation of p53 is the phosphorylation of its N-terminal domain. The N-terminal transcriptional activation domain contains a large number of phosphorylation sites and can be considered as the primary target for protein kinases transducing stress signals.

The protein kinases that are known to target this transcriptional activation domain of p53 can be roughly divided into two groups. A first group of protein kinases belongs to the MAPK family (JNK1-3, ERK1-2, p38 MAPK), which is known to respond to several types of stress, such as membrane damage, oxidative stress, osmotic shock, heat shock, etc. A second group of protein kinases (ATR, ATM, CHK1 and CHK2, DNA-PK, CAK) is implicated in the genome integrity checkpoint, a molecular cascade that detects and responds to several forms of DNA damage caused by genotoxic stress. Oncogenes also stimulate p53 activation, mediated by the protein p14ARF.

In unstressed cells, p53 levels are kept low through a continuous degradation of p53. A protein called Mdm2 (also called HDM2 in humans) binds to p53, preventing its action and transports it from the nucleus to the cytosol. Also Mdm2 acts as ubiquitin ligase and covalently attaches ubiquitin to p53 and thus marks p53 for degradation by the proteasome. However, ubiquitylation of p53 is reversible. A ubiqiutin specific protease, USP7 (or HAUSP), can cleave ubiquitin off p53, thereby protecting it from proteasome-dependent degradation. This is one means by which p53 is stabilized in response to oncogenic insults.

Phosphorylation of the N-terminal end of p53 by the above-mentioned protein kinases disrupts Mdm2-binding. Other proteins, such as Pin1, are then recruited to p53 and induce a conformational change in p53 which prevents Mdm2-binding even more. Phosphorylation also allows for binding of trancriptional coactivators, like p300 or PCAF, which then acetylate the carboxy-terminal end of p53, exposing the DNA binding domain of p53, allowing it to activate or repress specific genes. Deacetylase enzymes, such as Sirt1 and Sirt7, can deacetylate p53, leading to an inhibition of apoptosis. Some oncogenes can also stimulate the transcription of proteins which bind to MDM2 and inhibit its activity.

Assay Systems

The studies of the efficacy of Securolide in inducing selective cell death in Rad9 and/or p53 mutant yeast cell lines demonstrates the feasibility of using the cell lines to screen for other compounds that selectively induce cell death in Rad9 and/or p53 mutant lines as compared to the wild-type lines, or animal models. Suitable cell lines and animal models are commercially available or can be prepared with routine effort. For example, the American Type Culture Collection, Manassas, Va. 20108, lists several Rad9 mutant strains of yeast (catalog numbers 90731; 90730; 74154, 4003576, 4023576, and 4033576. A zebrafish containing a homologous cloned RAD9 is available from ATCC as catalog number 10169289. There are also numerous scientific publications on yeast strains that have various defects involving not just RAD9 and/or p53 but other aspects of the complex involving RAD9 and/or p53, which may also be used to screen for compounds that induce cell death as compared to normal cells. Normal cells, especially mammalian cells, can also be engineered to induce mutations into the hRAD9 and/or p53 gene, for use in assays. The human homolog is listed in the NCBI data base, along with the genes for mice and rats. (LocusID 5883).

Mutations are preferably introduced by site-directed mutagenesis. Site-directed mutagenesis is a molecular biology technique in which a mutation is created at a defined site in a DNA molecule. In general, site-directed mutagenesis requires that the wild-type gene sequence be known. An oligonucleotide with its sequence containing a desired mutation is chemically synthesized. The oligonucleotide is attached by base pair hydrogen bonding to the complementary wild-type gene sequence. The synthetic oligonucleotide is used as a primer for the in vitro synthesis of a new DNA strand that is complementary to the original (template) strand. The DNA synthesis is performed by adding the enzyme DNA polymerase to the DNA template. The newly synthesized strand of DNA has the primer and the desired mutation incorporated into it. By using a pair of primers and the polymerase chain reaction it is possible to amplify the newly created DNA molecule and produce enough copies to make further manipulation of the new DNA possible. Typically, the mutated DNA is then inserted into an expression vector by means of restriction enzymes and DNA ligase. The expression vector is then typically inserted into a cell where it can be used as a genetic template for the synthesis of a mutated protein. The biological activity of the mutated protein can then be compared to that of the wild-type protein.

Assays

In a preferred embodiment, the compound to be screened for activity is added to both normal (i.e., not having a deficiency in a checkpoint protein complex including Rad9 and/or a mutation in the p53 gene) and abnormal cells (i.e., having a mutation or inactivation in one or more of the proteins, or genes encoding the proteins, in the checkpoint protein complex including Rad9 and/or in p53). Those compounds which cause cell death in the abnormal cells as compared to the normal cells are then screened in further assays to assess general cytotoxicity and activity against specific cell types, such as tumor cells, bacterial cells, and virally infected cells.

Compounds

Suitable compounds which may exhibit anti-tumor activity through the selective targeting of the hRad9 and/or p53 gene in humans include:

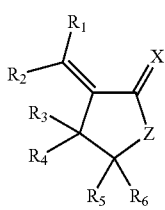

Formula Ia wherein $R_1$-$R_6$ taken independently or $R_3$-$R_6$ taken together are a hydrogen atom, a halogen atom, a hydroxyl group, or any other organic groupings containing any number of carbon atoms, preferably 1-8 carbon atoms, and optionally include a heteroatom such as oxygen, sulfur, or nitrogen grouping in linear, branched, or cyclic structural formats. $R_1$-$R_6$ may be substituted or unsubstituted.

$R_1$-$R_6$ are selected from alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C1-C20 cyclic, substituted C1-C20 cyclic, heterocyclic, substituted heterocyclic, aminoacid, peptide, or polypeptide group;

Z is a heteratom such as oxygen, sulfur, or nitrogen grouping in linear, branched, or cyclic structural formats; and X is a heteroatom such as oxygen, sulfur, or nitrogen grouping in linear, branched, or cyclic structural formats.

In another embodiment, the compound has the following chemical structure:

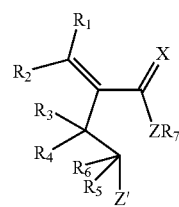

Formula Ib wherein $R_1$-$R_7$ taken independently or $R_3$-$R_6$ taken together may be a hydrogen atom, a halogen atom, a hydroxyl group, or any other organic groupings containing any number of carbon atoms, preferably 1-8 carbon atoms, and optionally include a heteroatom such as oxygen, sulfur, or nitrogen grouping in linear, branched, or cyclic structural formats, representative $R_1$-$R_6$ groupings being alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C1-C20 cyclic, substituted C1-C20 cyclic, heterocyclic, substituted heterocyclic, aminoacid, peptide, or polypeptide group;

X is a heteroatom such as oxygen, sulfur, or nitrogen grouping in linear, branched, or cyclic structural formats;

Z is a heteratom such as oxygen, sulfur, or nitrogen grouping in linear, branched, or cyclic structural formats; and Z' may a hydrogen atom, a halogen atom, a hydroxyl group, or any other organic composition containing from 1-8 carbon atoms and optionally include a heteroatom such as oxygen, sulfur, or nitrogen grouping in linear, branched, or cyclic structural formats.

In still another embodiment, the lactones having an alpha-methylene group can have the structure as show below:

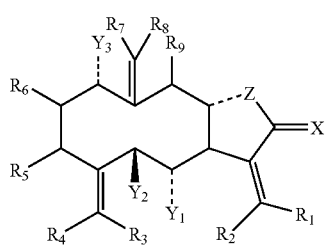

Formula Ic wherein $R_1$-$R_9$ taken independently or $R_5$ and $R_6$ taken together may be a hydrogen atom, a halogen atom, a hydroxyl group, or any other organic groupings containing any number of carbon atoms, preferably 1-8 carbon atoms, and optionally include a heteroatom such as oxygen, sulfur, or nitrogen grouping in linear, branched, or cyclic structural formats, representative $R_1$-$R_6$ groupings being alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C1-C20 cyclic, substituted C1-C20 cyclic, heterocyclic, substituted heterocyclic, aminoacid, peptide, or polypeptide group;

$Y_1$, $Y_2$, and $Y_3$ taken independently or $Y_1$ and $Y_2$ taken together may be a hydrogen atom, a halogen atom, a hydroxyl group, or any other organic groupings containing any number of carbon atoms, preferably 1-8 carbon atoms, and optionally include a heteroatom such as oxygen, sulfur, or nitrogen grouping in linear, branched, or cyclic structural formats, representative $R_1$-$R_6$ groupings being alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C1-C20 cyclic, substituted C1-C20 cyclic, heterocyclic, substituted heterocyclic, aminoacid, peptide, or polypeptide group;

Z is a heteratom such as oxygen, sulfur, or nitrogen grouping in linear, branched, or cyclic structural formats; and X is a heteratom such as oxygen, sulfur, or nitrogen grouping in linear, branched, or cyclic structural formats.

In one embodiment, the lactone is a securolide, which is a alpha-methylene-lactone (1) having the structure:

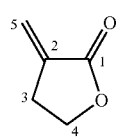

In another embodiment, the ester is methyl α-methylene-γ-hydroxy-butanoate (2) as shown in the following structure:

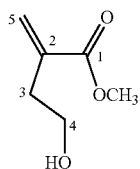

In still another embodiment, the lactone is a bicyclic compound having the following structure:

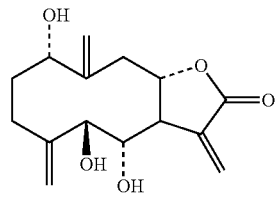

Other suitable compounds may include:

Formula Id

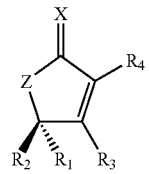

wherein
$R_1$-$R_4$ taken independently may be a hydrogen atom, a halogen atom, a hydroxyl group, or any other organic groupings containing any number of carbon atoms, preferably 1-8 carbon atoms, and optionally include a heteroatom such as oxygen, sulfur, or nitrogen grouping in linear, branched, or cyclic structural formats, representative $R_1$-$R_4$ groupings being H, alkyl, substituted alkyl, allyl, substituted allyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, alloxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C1-C20 cyclic, substituted C1-C20 cyclic, heterocyclic, substituted heterocyclic, aminoacid, peptide, or polypeptide group;

X is a heteroatom such as oxygen, sulfur, or nitrogen grouping in linear, branched, or cyclic structural formats; and Z is a heteratom such as oxygen, sulfur, or nitrogen grouping in linear, branched, or cyclic structural formats.

In still another embodiment, the lactones having an alpha-methylene group can have the structure as show below:

Formula Ie

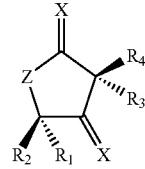

wherein
$R_1$-$R_4$ taken independently may be a hydrogen atom, a halogen atom, a hydroxyl group, or any other organic groupings containing any number of carbon atoms, preferably 1-8 carbon atoms, and optionally include a heteroatom such as oxygen, sulfur, or nitrogen grouping in linear, branched, or cyclic structural formats, representative $R_1$-$R_4$ groupings being alkyl, allyl, substituted alkyl, alkenyl, allyl, substituted allyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, alloxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C1-C20 cyclic, substituted C1-C20 cyclic, heterocyclic, substituted heterocyclic, aminoacid, peptide, or polypeptide group;

Z is a heteratom such as oxygen, sulfur, or nitrogen grouping in linear, branched, or cyclic structural formats; and X is a heteratom such as oxygen, sulfur, or nitrogen grouping in linear, branched, or cyclic structural formats.

Suitable compounds also include metabolites of the compounds described above, stereoisomers of the compounds described above, pharmaceutically acceptable salts thereof, and combinations thereof.

Representative lactones are listed in Table I:

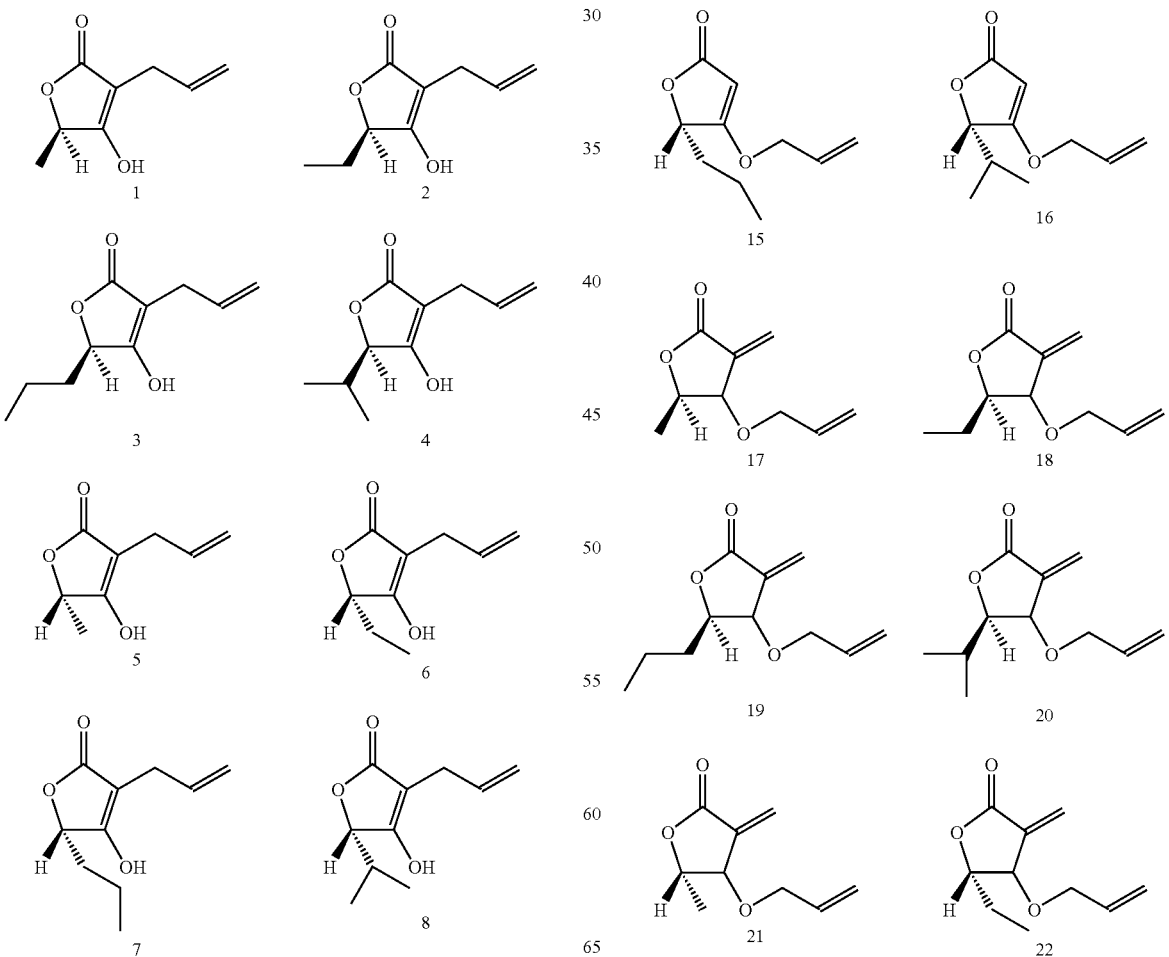

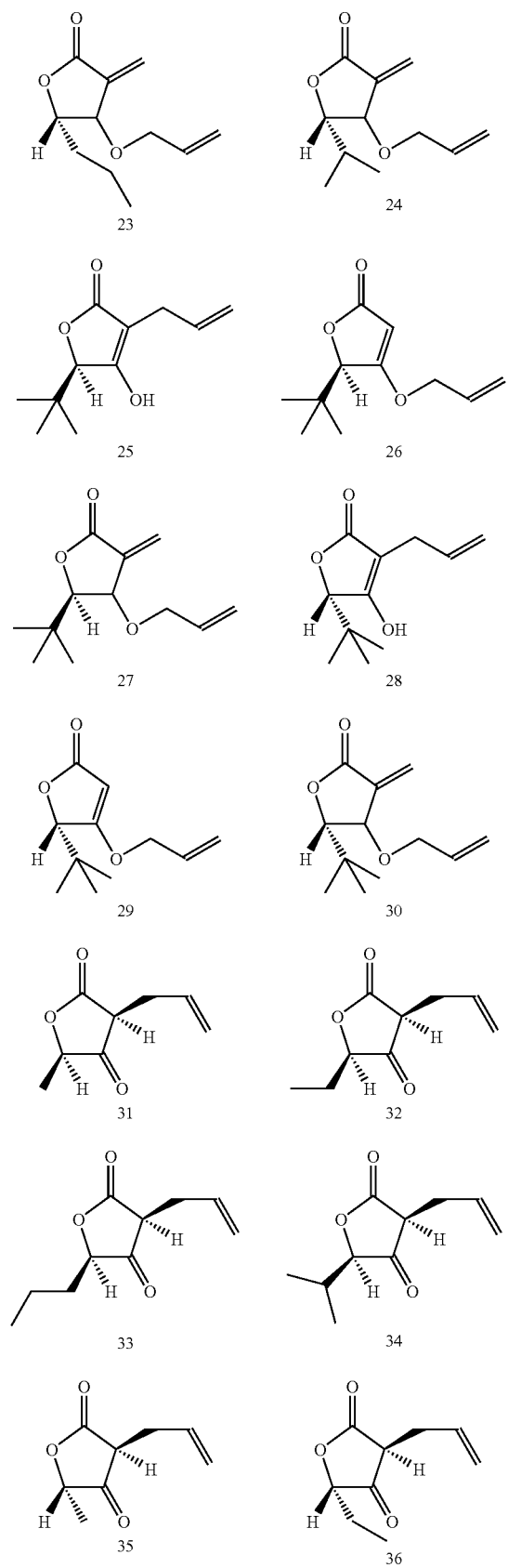
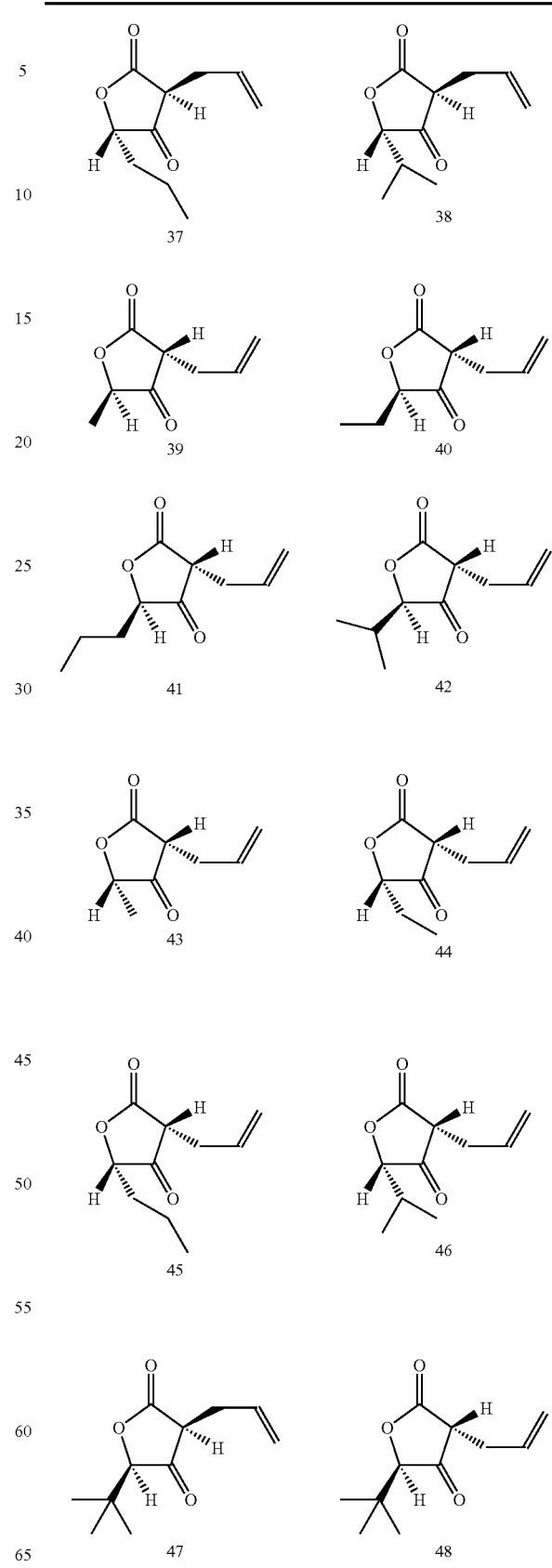

-continued

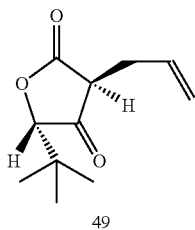

49

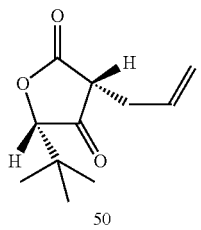

50

Pharmaceutically acceptable acid addition salts of compounds of formula Ia-Ie may be prepared in a conventional manner by treating a solution or suspension of the free base with about one chemical equivalent of a pharmaceutically acceptable acid. Conventional concentration and recrystallization techniques can be employed to isolate the salt.

The pharmaceutically acceptable base addition salts of compounds containing an acid group may be prepared in a conventional manner from the acid, e.g. by reaction with about one chemical equivalent of a base.

The present invention will be further understood by reference to following non-limiting examples.

EXAMPLE 1

Bioassay with Securolide on *Saccharomyces Cereviseae*

Bioassays on solid mediums were performed with Securolide (LMSV-6) in a concentration between ten and one hundred micrograms/milliliter on a set of mutant strains of *Saccharomyces cereviseae* with DNA similar to that in tumor/cancer cells. Securolide showed marked cytoxic activity only on the mutant strains, specifically the gene rad9. This indicates that Securolide has selective cytotoxicity to cells having unstable genomes.

We claim:

1. A method for screening for compounds having anti-cancer activity comprising (a) providing cells having one or more mutations in the cell cycle checkpoint protein complex that includes Rad9, wherein the cells have a mutation in the Rad9 gene, and wherein the cells are defective in the Rad9 protein-mediated cell cycle arrest, (b) adding a compound to be screened to the cells, wherein the compound has the structure of Formula Ia:

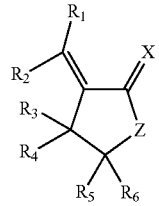

Formula Ia wherein $R_1$-$R_6$ independently are selected from a hydrogen atom, a halogen atom, a hydroxyl group, alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, phenoxy, substituted phenoxy, aroxy, substituted aroxy, alkylthio, phenylthio, substituted phenylthio, arylthio, substituted arylthio, cyano, isocyano, substituted isocyano, carbonyl, carboxyl, substituted carboxyl, amino, substituted amino, amido, substituted amido, sulfonyl, sulfonic acid, phosphoryl, phosphonyl, polyaryl, substituted polyaryl, $C_3$-$C_{20}$ cyclic, substituted $C_1$-$C_{20}$ cyclic, heterocyclic, substituted heterocyclic, an amino acid, a peptide, or a polypeptide group; or $R_3$-$R_6$ taken together form a substituted or unsubstituted ring that optionally includes one or more heteroatoms selected from the group consisting of oxygen, sulfur, and nitrogen;

Z is a heteroatom selected from oxygen, sulfur, or nitrogen; and

X is a heteroatom selected from oxygen, sulfur, or nitrogen (c) determining if the compound kills or induces apoptosis in some or all of the cells;

(d) comparing the resultant determination of step (c) to the resultant determination induced by the compound in normal cells not having the one or more mutations in (a) to determine if the compound has anti-cancer activity.

2. The method of claim 1 wherein the cells are yeast cells.

3. The method of claim 1 wherein the cells are mammalian cells.

4. The method of claim 3, wherein the method is an in vitro assay.

5. The method of claim 1 wherein the cells are tumor cells.

6. The method of claim 1 wherein the cells have an inactive or less active Rad9 protein.

* * * * *

UNITED STATES PATENT AND TRADEMARK OFFICE
CERTIFICATE OF CORRECTION

PATENT NO. : 8,501,431 B2
APPLICATION NO. : 12/605896
DATED : August 6, 2013
INVENTOR(S) : David Terrero et al.

It is certified that error appears in the above-identified patent and that said Letters Patent is hereby corrected as shown below:

In the Claims

Claim 1, column 16, line 27, replace "substituted $C_1$-$C_{20}$ cyclic" with --substituted $C_3$-$C_{20}$ cyclic--

Signed and Sealed this
Nineteenth Day of November, 2013

Teresa Stanek Rea
*Deputy Director of the United States Patent and Trademark Office*